U S010292891B2

(12) United States Patent
Zheng et al.

(10) Patent No.: US 10,292,891 B2
(45) Date of Patent: May 21, 2019

(54) ACTIVE ROBOTIC WALKER AND ASSOCIATED METHOD

(71) Applicant: Ohio State Innovation Foundation, Columbus, OH (US)

(72) Inventors: Yuan Fang Zheng, Columbus, OH (US); Hongfei Wang, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/937,186

(22) Filed: Mar. 27, 2018

(65) Prior Publication Data

US 2018/0344560 A1    Dec. 6, 2018

Related U.S. Application Data

(60) Provisional application No. 62/514,201, filed on Jun. 2, 2017.

(51) Int. Cl.
*A61H 3/04* (2006.01)
*A61H 1/02* (2006.01)
(Continued)

(52) U.S. Cl.
CPC ......... *A61H 1/0262* (2013.01); *A61F 5/0123* (2013.01); *A61H 3/00* (2013.01);
(Continued)

(58) Field of Classification Search
CPC .............. A61H 3/04; A61H 2203/0406; A61H 2203/0403; A61H 2201/1207;
(Continued)

(56) References Cited

U.S. PATENT DOCUMENTS 1,878,785 A * 9/1932 Leavitt ................. A61G 7/1015
5/310
4,254,948 A   3/1981 Jacobs
(Continued)

FOREIGN PATENT DOCUMENTS

CN  101947177 A  1/2011
CN  103908393 A  7/2014
(Continued)

OTHER PUBLICATIONS

European Patent Office: International Search Report and Written Opinion in related International Patent Application No. PCT/US2018/024569 dated Oct. 4, 2018; 23 pages.

*Primary Examiner* — Erez Gurari
(74) *Attorney, Agent, or Firm* — Wood Herron & Evans LLP (57) ABSTRACT

A robotic walker and associated method are provided. The robotic walker includes a housing containing a control unit operatively connected to a drive unit. The drive unit is operatively connected to a pair of motorized drive wheels. The robotic walker includes first and second winches, each winch having a strap that can be retracted by its respective winch, each winch is operatively connected to the drive unit, each strap having an end adapted to be removably connected to a pair of leg braces worn by a user. The first and second winches may retract a portion of each respective strap to move the legs of the user forward. A first control button is operatively connected to the control unit. The control unit is configured to operate the robotic walker in at least one control mode and the first control button being operable to start the at least one control mode.

17 Claims, 11 Drawing Sheets

(51) Int. Cl.
   *A61H 3/00* (2006.01)
   *A61H 3/02* (2006.01)
   *A61F 5/01* (2006.01)
(52) U.S. Cl.
   CPC .............. *A61H 3/02* (2013.01); *A61H 3/04* (2013.01); *A61H 2003/007* (2013.01); *A61H 2003/043* (2013.01); *A61H 2201/0173* (2013.01); *A61H 2201/1207* (2013.01); *A61H 2201/1215* (2013.01); *A61H 2201/14* (2013.01); *A61H 2201/149* (2013.01); *A61H 2201/164* (2013.01); *A61H 2201/165* (2013.01); *A61H 2201/1635* (2013.01); *A61H 2201/1642* (2013.01); *A61H 2201/1652* (2013.01); *A61H 2201/5007* (2013.01); *A61H 2201/5025* (2013.01); *A61H 2201/5035* (2013.01); *A61H 2201/5066* (2013.01); *A61H 2203/0406* (2013.01); *A61H 2205/106* (2013.01)
(58) Field of Classification Search
   CPC .... A61H 2201/5007; A61H 2201/5025; A61H 2201/1642; A61H 2201/121; A61H 2201/0173; A61H 2201/165; A61H 2003/007; A61H 2003/043
   See application file for complete search history.

(56) References Cited

U.S. PATENT DOCUMENTS

| | | | | |
|---|---|---|---|---|
| 4,985,947 A * | 1/1991 | Ethridge | ............ | A61G 7/1017 280/250.1 |
| 5,333,333 A * | 8/1994 | Mah | ............ | A61G 5/10 280/250.1 |
| 5,732,964 A * | 3/1998 | Durham | ............ | A61H 3/04 135/67 |
| 6,289,534 B1 * | 9/2001 | Hakamiun | ............ | A61G 7/1017 5/83.1 |
| 6,643,869 B1 * | 11/2003 | Sloan, Jr. | ............ | A61G 7/10 280/304.1 |
| 7,150,722 B1 * | 12/2006 | Tyrrell | ............ | A61H 3/008 602/23 |
| 7,294,094 B1 * | 11/2007 | Howle | ............ | A61H 3/00 135/67 |
| 9,554,964 B1 * | 1/2017 | Johnson | ............ | A61H 9/0078 |
| 2010/0170546 A1 * | 7/2010 | Popovic | ............ | A61H 3/008 135/67 |
| 2010/0270771 A1 * | 10/2010 | Kobayashi | ............ | A61H 3/008 280/210 |
| 2011/0275043 A1 * | 11/2011 | Liu | ............ | A61H 1/024 434/247 |
| 2012/0042917 A1 * | 2/2012 | Workman | ............ | A61H 3/008 135/66 |
| 2013/0098413 A1 * | 4/2013 | Ahlbertz | ............ | A61G 7/1019 135/66 |
| 2013/0221716 A1 * | 8/2013 | Purwar | ............ | A61G 7/1017 297/311 |
| 2014/0026893 A1 * | 1/2014 | Johnson | ............ | A61H 3/008 128/845 |
| 2014/0196757 A1 | 7/2014 | Goffer | | |
| 2014/0276306 A1 * | 9/2014 | Dreske | ............ | A61H 3/008 602/19 |
| 2015/0182408 A1 * | 7/2015 | Roh | ............ | A61H 3/00 482/51 |
| 2015/0250675 A1 * | 9/2015 | Kalinowski | ............ | A61H 3/008 482/69 |
| 2015/0342822 A1 * | 12/2015 | Osterhaus | ............ | A61H 3/04 280/657 |
| 2016/0158088 A1 * | 6/2016 | Frankian | ............ | A61H 3/04 482/69 |
| 2017/0001656 A1 * | 1/2017 | Katayama | ............ | B62B 5/0069 |
| 2017/0028242 A1 * | 2/2017 | Miyoshi | ............ | A61H 7/001 |
| 2018/0177665 A1 * | 6/2018 | Rogozinski | ............ | A61H 1/0262 |

FOREIGN PATENT DOCUMENTS

| | | |
|---|---|---|
| GB | 2484463 A | 4/2012 |
| JP | 2003 205002 A | 7/2003 |
| JP | 2011 072506 A | 4/2011 |
| KR | 101 104 065 B1 | 1/2012 |
| WO | 2008/096210 A1 | 8/2008 |
| WO | 2015/120186 A1 | 8/2015 |
| WO | 2017/078576 A1 | 5/2017 |

* cited by examiner

ACTIVE ROBOTIC WALKER AND ASSOCIATED METHOD

RELATED APPLICATION

This application claims priority to U.S. Provisional Patent Application Ser. No. 62/514,201 filed Jun. 2, 2017, the disclosure of which is expressly incorporated by reference herein in its entirety.

FIELD OF THE INVENTION

This invention generally relates to a walker, and more particularly to an active robotic walker.

BACKGROUND OF THE INVENTION

Many humans suffer from poor mobility. For example, some people may be unable to walk, such as paraplegics. Others may be in a weakened state and thus have minimal ability to walk. Still others may be healthy but may become fatigued after walking a certain distance.

Exoskeletons have been developed in order to provide power to human leg joints to mobilize a user's legs. However, exoskeletons are heavy, bulky, complicated, and expensive.

Accordingly, there is a need for improved systems and methods for mobilizing a user's legs.

SUMMARY OF THE INVENTION

Embodiments of the invention are directed to a robotic walker, a method for moving a user strapped to a robotic walker, and a walking assistant.

In an embodiment of the invention, a robotic walker is provided. The robotic walker includes a frame having a front and a back; a pair of motorized drive wheels configured to support the front of the frame; a pair of wheels configured to support the back of the frame; a housing mounted on the frame, the housing containing a control unit operatively connected to a drive unit, the housing further containing a power supply operatively connected to the control unit and the drive unit; the drive unit being operatively connected to the pair of motorized drive wheels; first and second winches mounted on the frame, each first and second winch having a strap that can be retracted by its respective winch, each winch being operatively connected to the drive unit, each strap having an end adapted to be removably connected to a pair of leg braces worn by a user; and a first control button operatively connected to the control unit. The control unit is configured to operate the robotic walker in at least one control mode and the first control button being operable to start the at least one control mode.

In another embodiment of the invention, a method is provided for moving a user strapped to a robotic walker, where the robotic walker includes a pair of motorized drive wheels, a control unit configured to operate the robotic walker in at least one control mode, a first control button operable to start the at least one control mode, first and second winches, each winch having a retractable strap with an end being removably connected to a pair of leg braces worn by the user. The method includes actuating the first control button to start the at least one control mode; energizing the first winch to retract a portion of its respective strap so as to move one leg of the user forward; energizing the second winch to retract a portion of its respective strap so as to move the other leg of the user forward; and energizing the motorized drive wheels to move the robotic walker forward a predetermined distance.

In another embodiment of the invention a walking system to assist a user to walk is provided. The walking system includes left and right crutches, where each crutch includes a housing mounted to a bottom portion of the crutch, the housing containing a control unit operatively connected to a drive unit, the housing further containing a power supply operatively connected to the control unit and the drive unit; a winch mounted to the bottom portion of the crutch, the winch having a retractable strap, the winch being operatively connected to the drive unit, the strap having an end adapted to be removably connected to a leg strap on the user's leg; a control button positioned to be actuated by the user's hand, the control button operatively connected to the control unit. The control unit is configured to operate the crutch in at least one control mode and the control button being operable to start the at least one control mode.

The above summary presents a simplified overview of some embodiments of the invention to provide a basic understanding of certain aspects of the invention discussed herein. The summary is not intended to provide an extensive overview of the invention, nor is it intended to identify any key or critical elements, or delineate the scope of the invention. The sole purpose of the summary is merely to present some concepts in a simplified form as an introduction to the detailed description presented below.

BRIEF DESCRIPTION OF THE DRAWINGS

The accompanying drawings, which are incorporated in and constitute a part of this specification, illustrate embodiments of the invention and, together with the detailed description of the embodiments given below, serve to explain the principles of the invention.

DETAILED DESCRIPTION OF THE INVENTION

Figure 1:
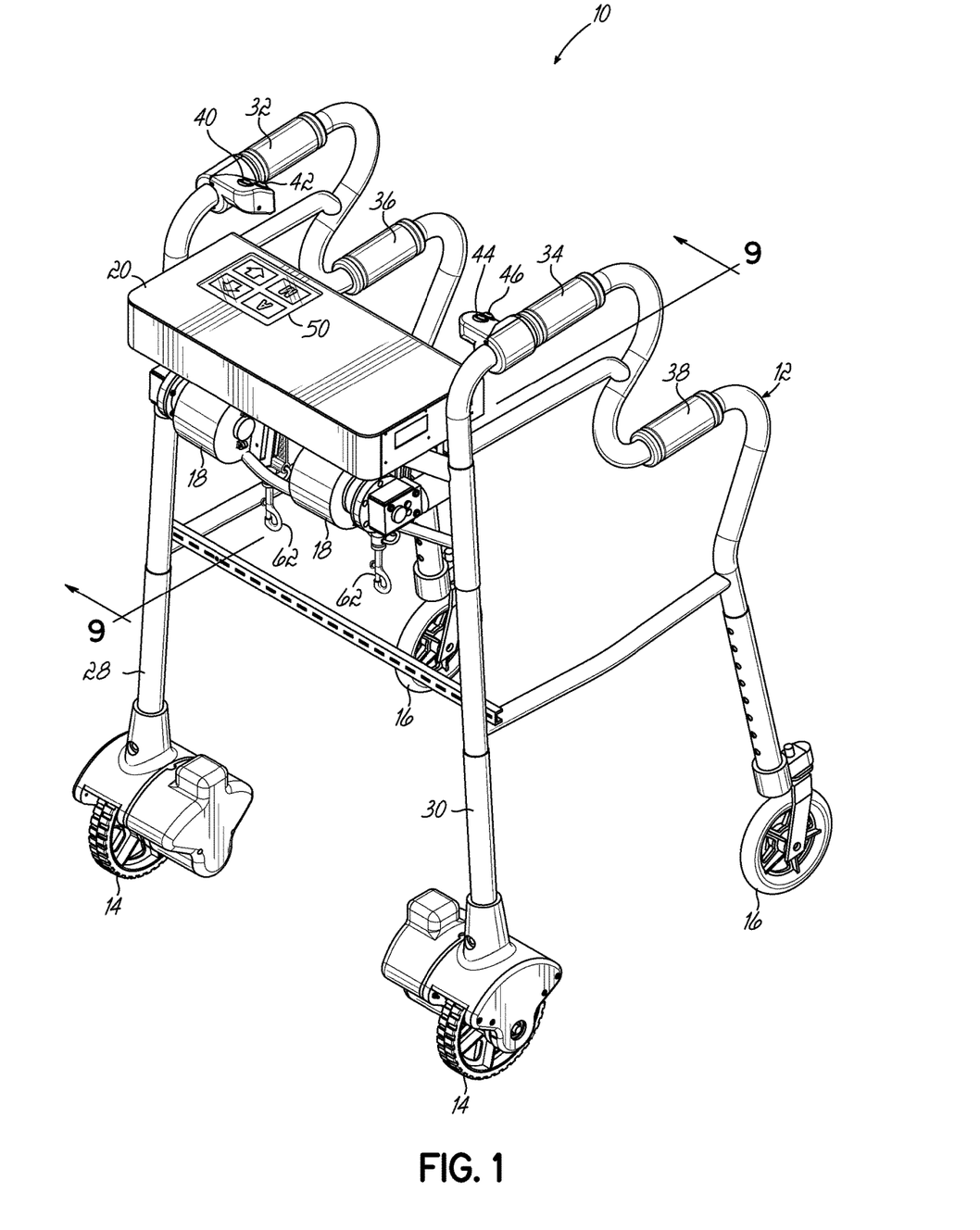
FIG. 1 is a perspective view of a robotic walker in accordance with an embodiment of the invention.
Figure 2:
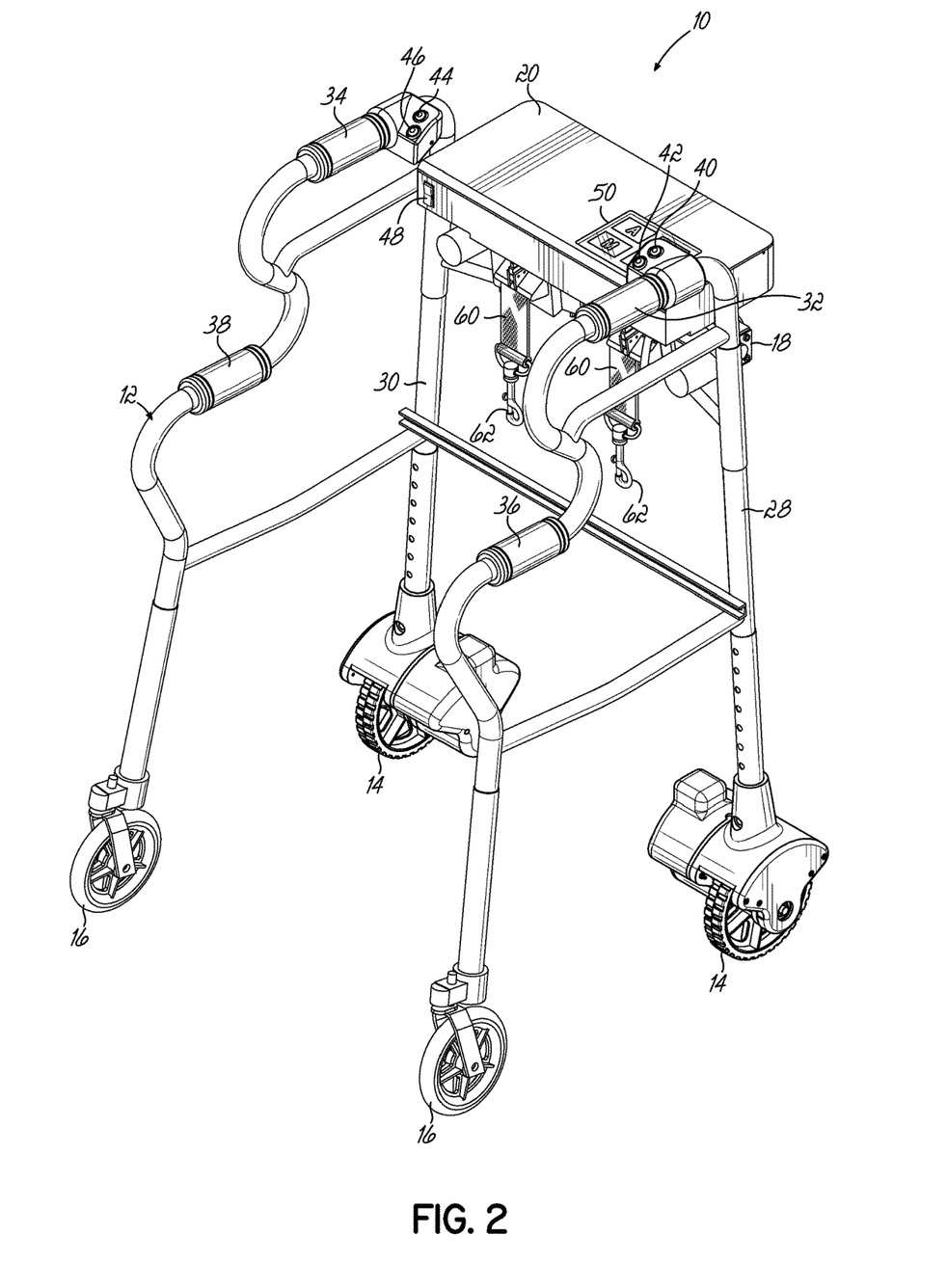
FIG. 2 is a perspective view of the robotic walker of FIG. 1.
Figure 3:
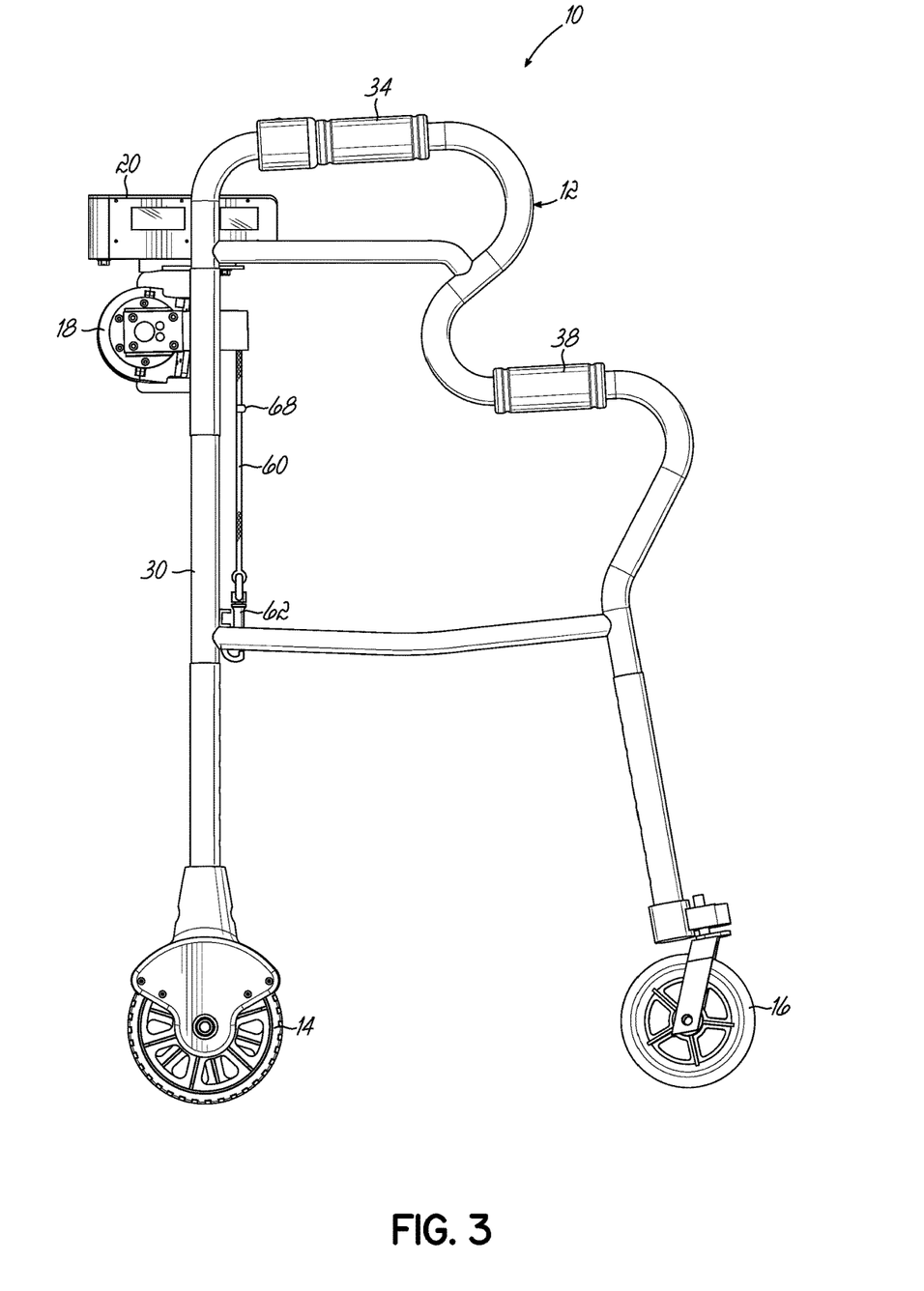
FIG. 3 is a side view of the robotic walker of FIG. 1.
Figure 4:
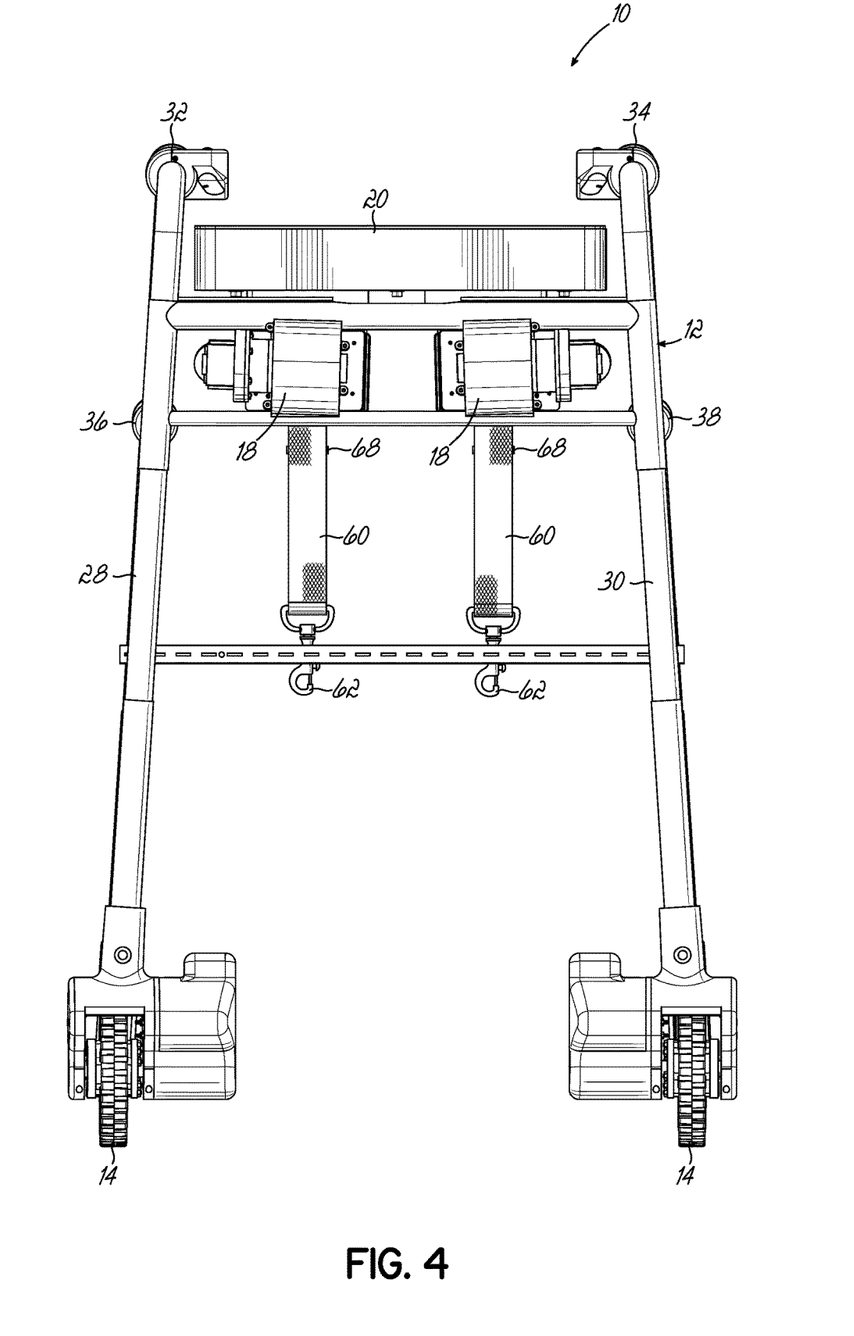
FIG. 4 is a front view of the robotic walker of FIG. 1.
Figure 5:
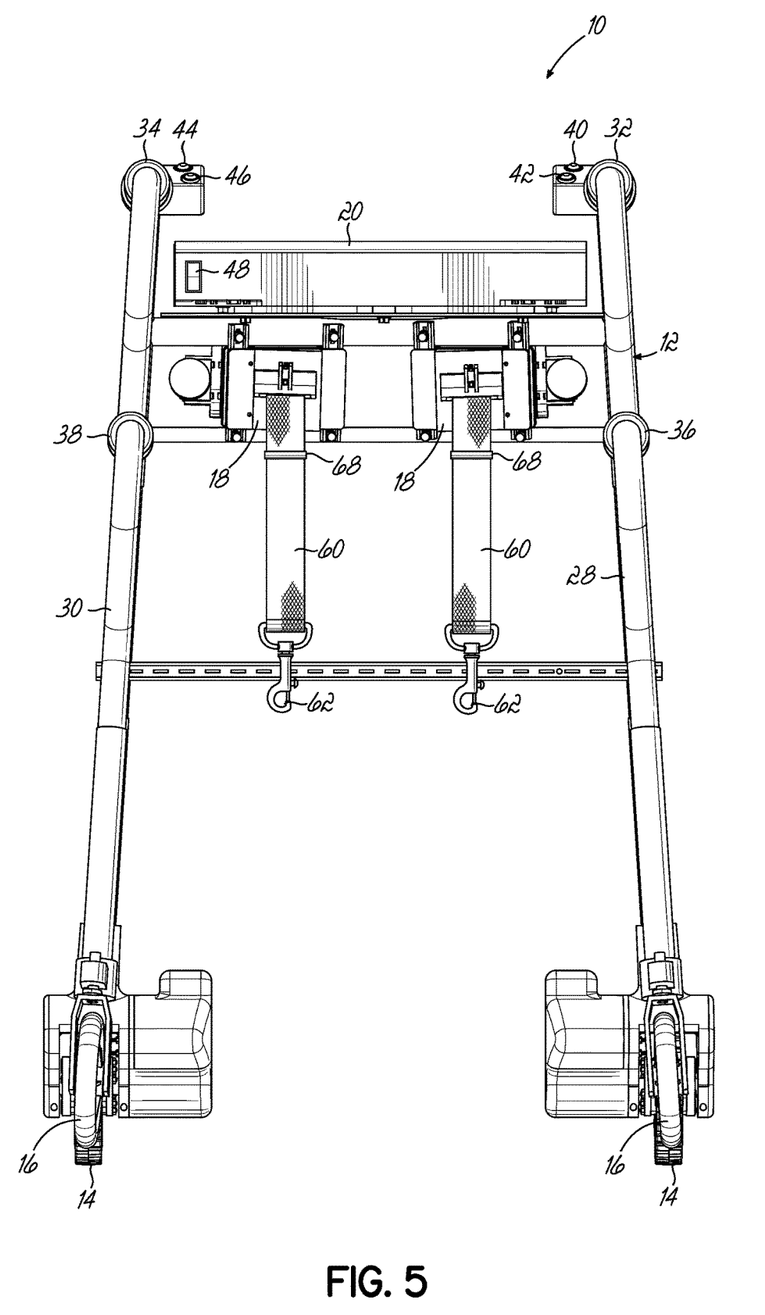
FIG. 5 is a rear view of the robotic walker of FIG. 1.
Figure 6:
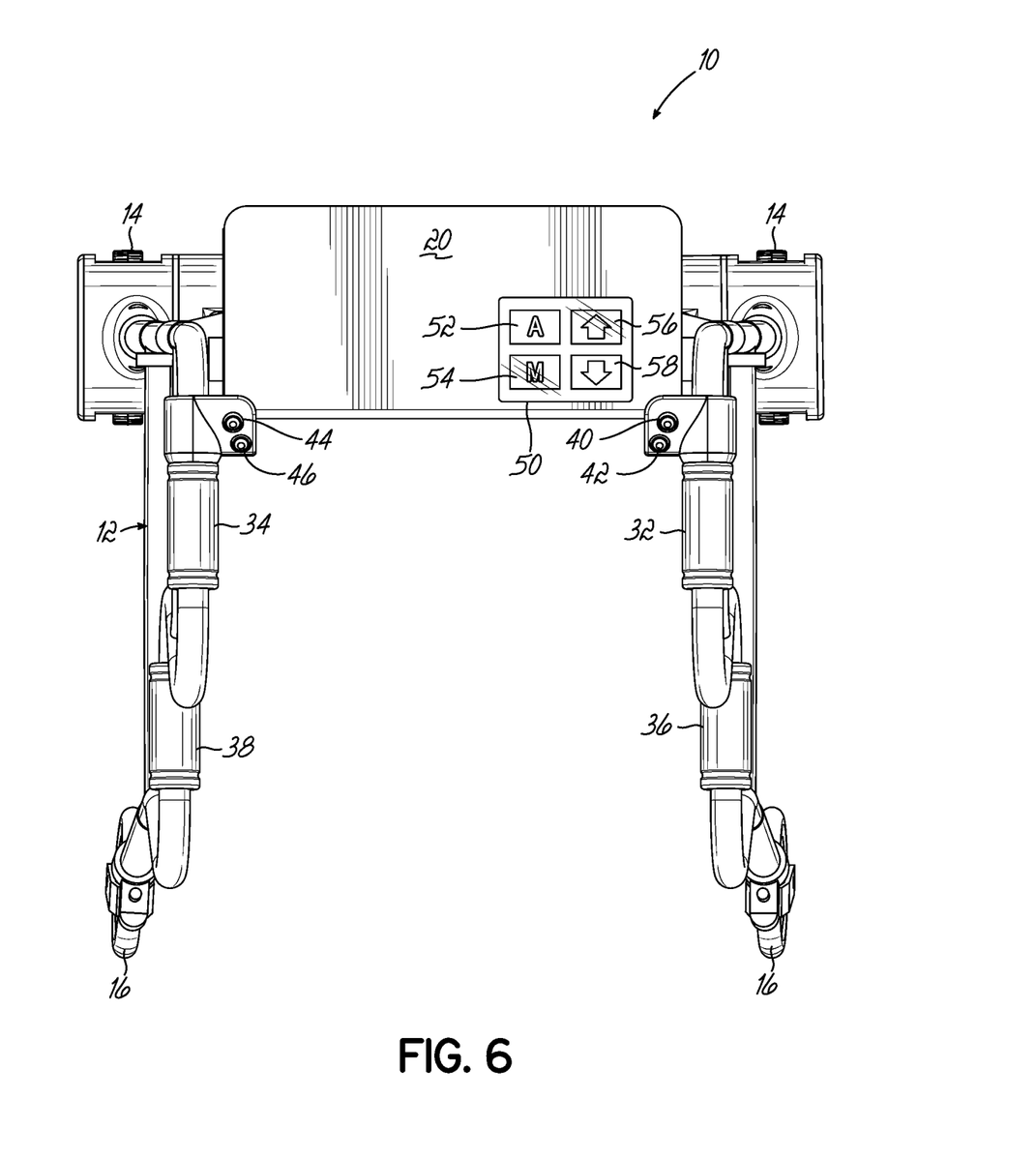
FIG. 6 is a top view of the robotic walker of FIG. 1.
Figure 7:
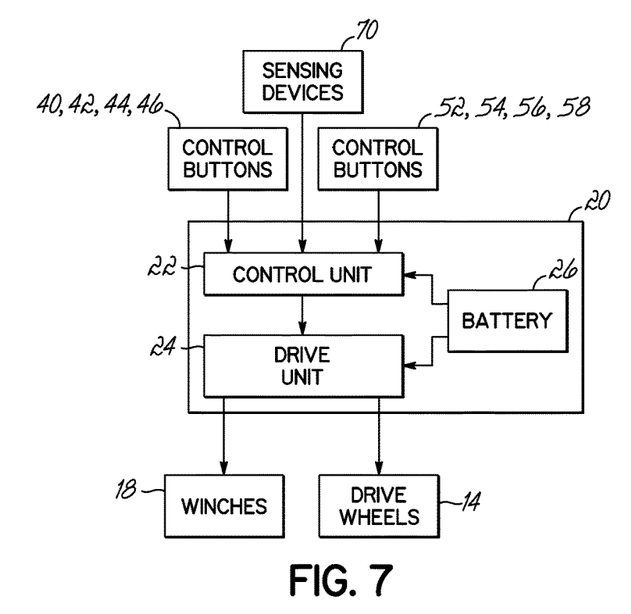
FIG. 7 is a schematic representation of the control system of the robotic walker of FIG. 1.
Figure 8:
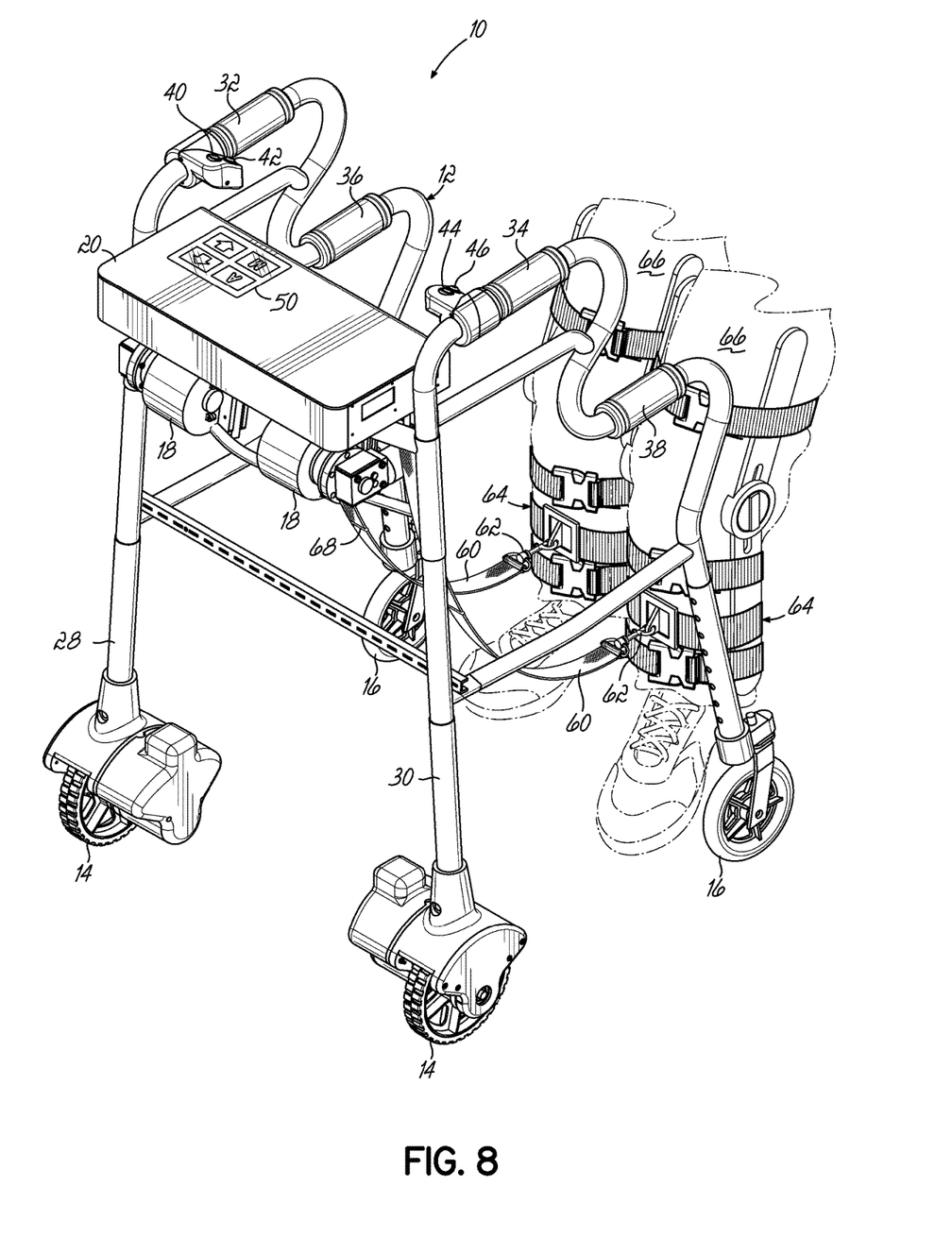
FIG. 8 is a perspective view of the robotic walker of FIG. 1 connected to a user's legs.

A robotic walker 10 in accordance with one embodiment of the invention is shown FIGS. 1-6. FIG. 8 shows the robotic walker 10 being used by user. Any reference to the left, right, front (forward), or back (rear) of the robotic walker 10 (or any other described embodiment) corresponds to the left, right, front, or back of the user. For example, any reference to the right side of the robotic walker 10 is on the right side of the user. The robotic walker 10 includes a frame 12 supported by a pair of motorized drive wheels 14 and a pair of non-motorized wheels 16. The robotic walker 10 further includes a pair of pulleys or winches 18 mounted on the frame 12. The robotic walker 10 also includes a housing 20 mounted on the frame 12. As shown in FIG. 7, the housing 20 includes a control unit 22, a drive unit 24, both of which are electrically coupled to a power supply 26, such as a battery. The control unit 22 contains at least one microprocessor (not shown) and in some embodiments may contain at least three microprocessors to operate the robotic walker 10 in at least one control mode. The microprocessors run the software which is used to control the motions of the motorized drive wheels 14 and the winches 18. The drive unit 24 is a power amplifier which receives command signals from the microprocessors in the control unit 22 and then sends power to the motorized drive wheels 14 and winches 18 as commanded. In the embodiment shown in FIGS. 1-6, there is a power cable running between the drive unit 24 and the motorized drive wheels 14, which is hidden within front down tubes 28, 30 of the frame 12.

The frame 12 includes upper hand grips 32, 34 and lower hand grips 36, 38. A front control button 40 and a rear control button 42 are associated with the upper hand grip 32. Similarly, a front control button 44 and a rear control button 46 are associated with the upper hand grip 34. Control button 40 is coupled to the control unit 22 such that when it is actuated it commands the control unit 22 to start a particular control mode. Control button 44 is coupled to the control until 22 such that when it is actuated it commands the control unit 22 to stop the current control mode. Control button 42 may act as an emergency stop. Control button 46 may be used to control the speed of the motorized drive wheels 14 and winches 18. The arrangement and control functionality of the control buttons 40, 42, 44, 46 may be altered according to how the control unit 22 is wired. For example, control button 44 could be wired to be the start button and control button 40 could be wired to be the stop button. Further, the robotic walker 10 could have only two control buttons (e.g., only start and stop) or additional control buttons if additional control functionality is required. In the embodiment of FIGS. 1-6, the control buttons 40, 42, 44, 46 are push buttons, but the control buttons 40, 42, 44, and 46 could be in other form of control device adapted to send command signals to the control unit 22, such as toggle switches, dials, thumbwheels, or rocker switches, for example. The housing 20 also includes an on-off button 48 which is configured to enable or disable power from the battery 26 to the control unit 22 and the drive unit 24.

When the user puts the on-off button 48 in the on position, a touch screen control panel 50 powers up. In addition, the control unit 22 performs a calibration routine such that each winch 18 lets out a predetermined length for each strap 60. In the embodiment of the touch screen control panel 50 shown in FIG. 6, the touch screen control panel 50 has four touch-activated buttons 52, 54, 56, 58, which are operatively connected to control unit 22. Touch-activated button 52 activates an automatic control mode for the robotic walker 10. Touch-activated button 54 activates a manual control mode of operation for the robotic walker 10. The automatic and manual control modes will be explained below. When actuated, touch-activated button 56 energizes the motorized drive wheels 14, causing the robotic walker 10 to move forward and when actuated, touch-activated button 58 energizes the motorized drive wheels 14 in the opposite direction, causing the robotic walker 10 to move backward. Winches 18 do not move when either touch-activated button 56 or touch-activated button 58 is pushed. In other words, touch-activated buttons 56, 58 are used solely to move the robotic walker 10 forwards and backwards.

Figure 9:
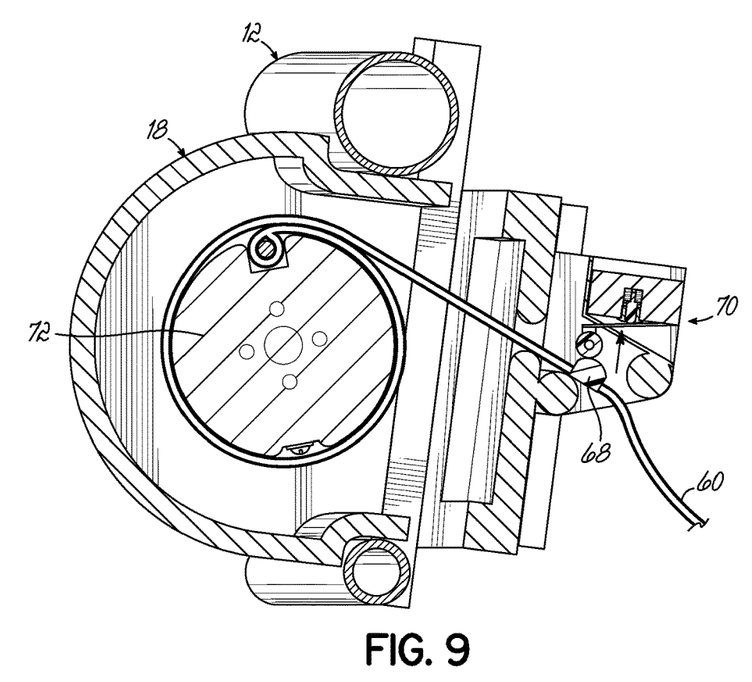
FIG. 9 is a cross-sectional view of the robotic walker of FIG. 1 taken along line 9-9.

As shown in FIGS. 8-9, the robotic walker 10 includes two straps 60 operatively coupled to winches 18. The free end of each strap 60 has a quick disconnect hook 62 that is configured to be removably connected to the lower section of a pair of leg braces 64 strapped to the left and right legs 66 of a user of the robotic walker 10. Each strap 60 further includes a stop-motion limit member 68 (FIGS. 5, 9) configured to interact with sensing devices, such as limit switches 70 (FIG. 9), one associated with each winch 18. As the winches 18 retract the straps 60 around spools 72, the stop-motion limit members 68 engages the respective limit switches 70, which sends a signal to the control unit 22 (FIG. 7), which causing the drive unit 24 to interrupt the power to winches 18 such that the winches 18 immediately stop retracting the straps 60 around the spools 72.

Figure 10:
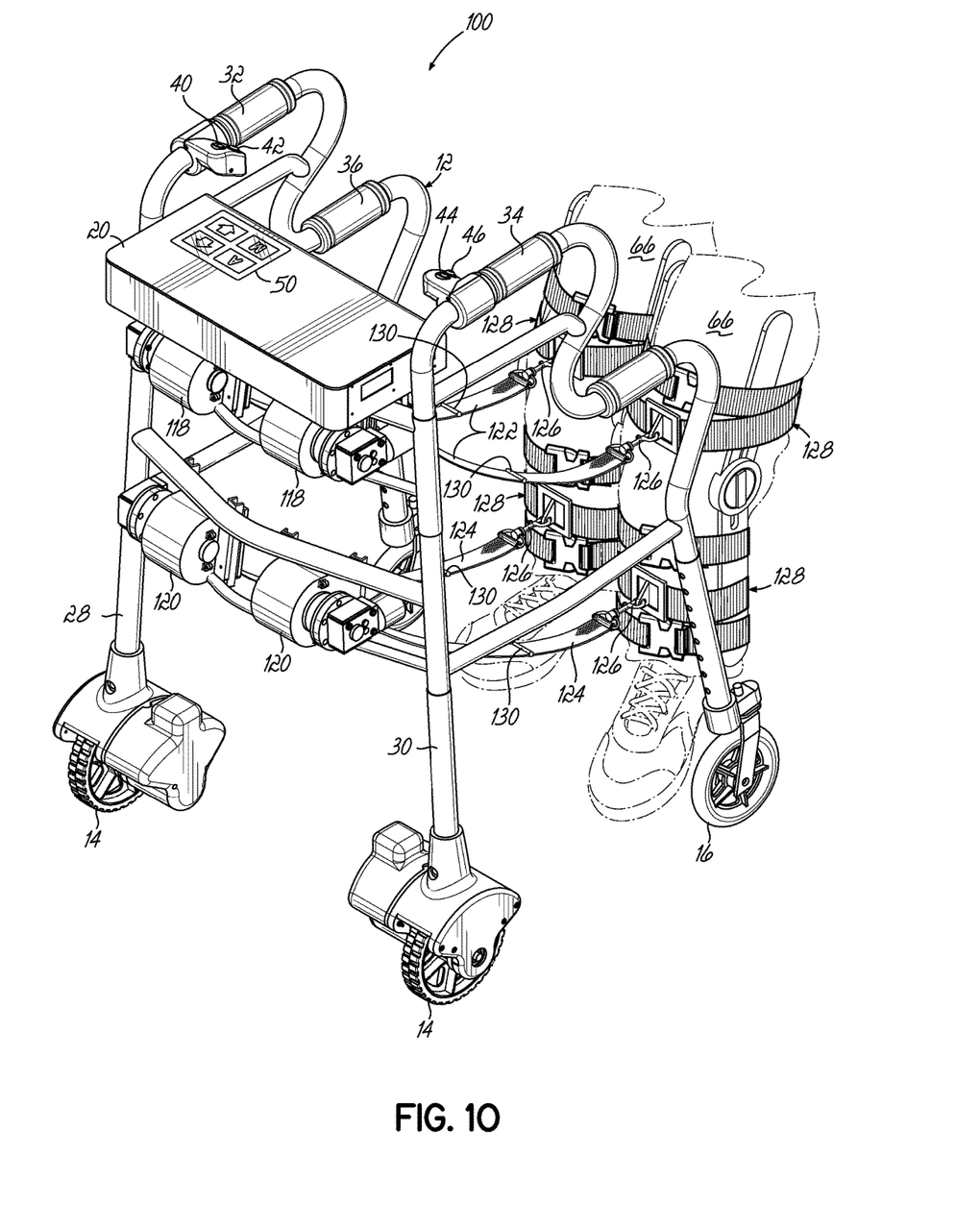
FIG. 10 is a perspective view of a robotic walker in accordance with another embodiment of the invention connected to a user's legs.

A robotic walker 100 in accordance with another embodiment of the invention is shown in FIG. 10. The robotic walker 100 is similar in structure and operation to robotic walker 10. As such, only the pertinent structural differences of robotic walker 100 are described. Robotic walker 100 has two upper winches 118 and two lower winches 120 instead of just the two winches 18 of robotic walker 10. Two upper straps 122 are operatively coupled to upper winches 118 and two lower straps 124 are operatively coupled to lower winches 120. The free end of each of the straps 122, 124 includes a quick disconnect hook 126. The hooks 126 on the upper straps 122 are configured to be removably connected to the upper section of a pair of leg braces 128 strapped to the left and right legs 66 of a user of the robotic walker 100. Similarly, the hooks 126 on the lower straps 122 are configured to be removably connected to the lower sections of leg braces 128. The upper and lower straps 122, 124 further include stop-motion limit members 130 that are configured to engage limit switches 70 (not shown in FIG. 10) associated with upper and lower winches 118, 120.

To use the robotic walker 10, a user wearing leg braces 64 would stand at the back of the robotic walker 10 near the rear of the frame 12. The user would put the on-off button 48 in the on position, which would turn on the touch screen control panel 50 and cause the control unit 22 to perform the calibration routine. The user would connect straps 60 to the lower section of the leg brace 64. The user can then select either automatic control mode by actuating touch-activated button 52 or manual control mode by actuating touch-activated button 54. If the user selects the automatic control mode, the user would then actuate control button 40, i.e., the start button. The winch 18 on the right side of the robotic walker 10 is energized and retracts a portion of the right strap 60 which is connected to the leg brace 64 on the user's right leg. When the stop-motion limit member 68 on the right strap 60 engages the limit switch 70 associated with the right winch 18, the right winch 18 stops and then releases a portion of the right strap 60 to allow the right foot to move down and contact the surface (e.g., the floor), thereby completing the right step. The left winch 18 is then energized and retracts a portion of the left strap 60 which is connected to the leg brace 64 on the user's left leg. When the stop-motion limit member 68 on the left strap 60 engages the limit switch 70 associated with the left winch 18, the left winch 18 stops and then releases a portion of the left strap 60 to allow the left foot to move down and contact the surface (e.g., the floor), thereby completing the left step. The motorized drive wheels 14 then move the walker forward a predetermined distance and simultaneously the winches 18 let out the same length of strap. This completes a full step cycle of the automatic control mode. The robotic walker 10 will repeat this step cycle of events to move the user and the robotic walker 10 forward until the user actuates control button 44, i.e., the stop button. The automatic step cycle can be interrupted at anytime by the user by actuating control button 44.

If the user selects the manual control mode, the user will actuate control button 40 to start a step cycle. The robotic walker 10 will complete one step cycle as described above, but the robotic walker 10 will not repeat that cycle of events automatically. Should the user want the robotic walker 10 to complete an additional step cycle, the user would actuate control button 40 to start the step cycle again. The manual step cycle can be interrupted by actuating control button 44.

The operation of the robotic walker 100 with the four winches 118, 120 is generally the same as the operation explained above for the robotic walker 10. During a step cycle, both right side winches 118, 120 will work together to pull the right leg of the user forward and both left side winches 118, 120 will work together to pull the left leg of the user forward. The initiation of the pulling of winches 120 may slightly lag the initiation of the pulling of winches 118 by short period, such as a fraction of a second.

Figure 11:
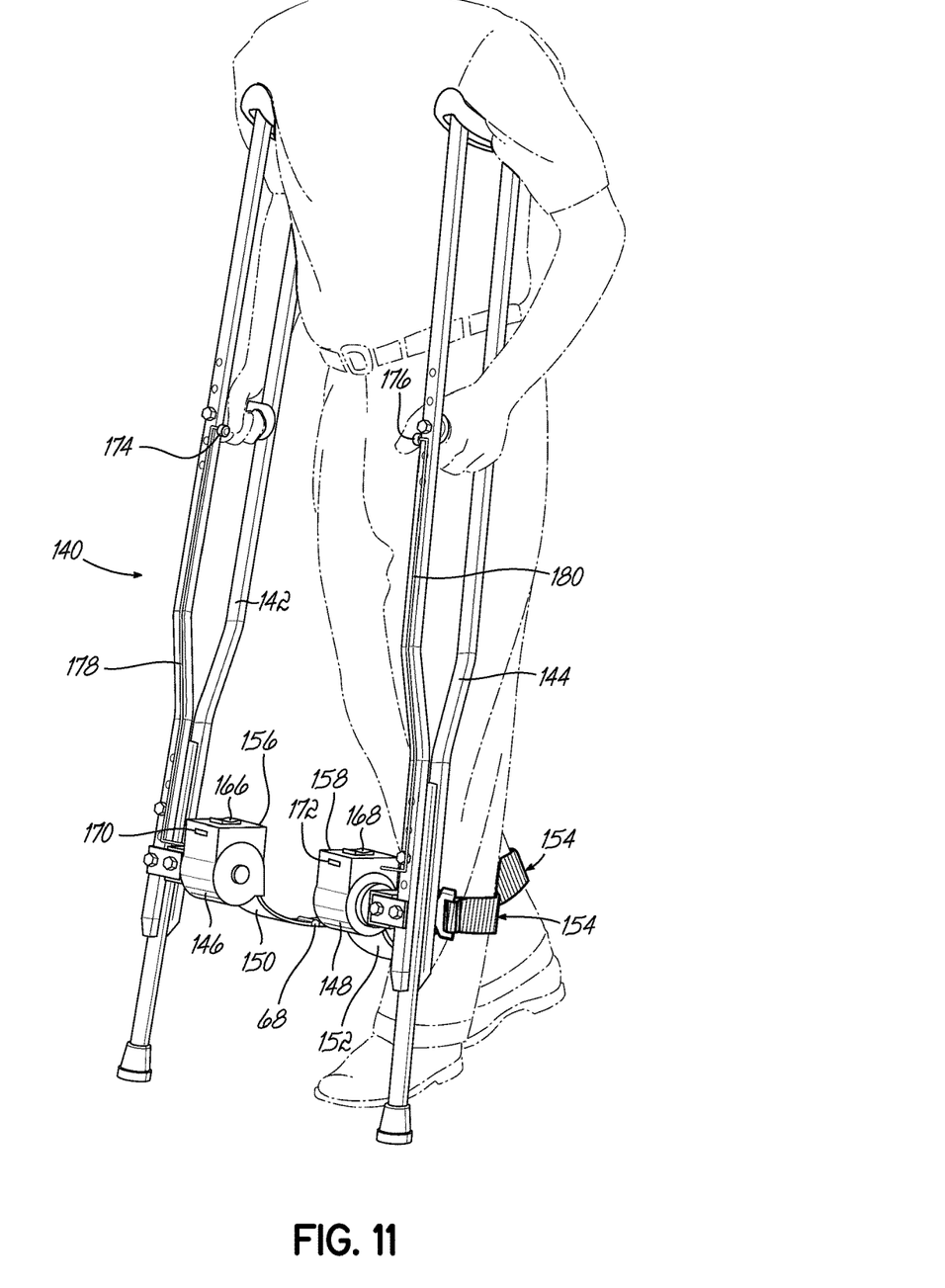
FIG. 11 is a perspective view of winch assisted crutches in accordance with another embodiment of the invention.
Figure 12:
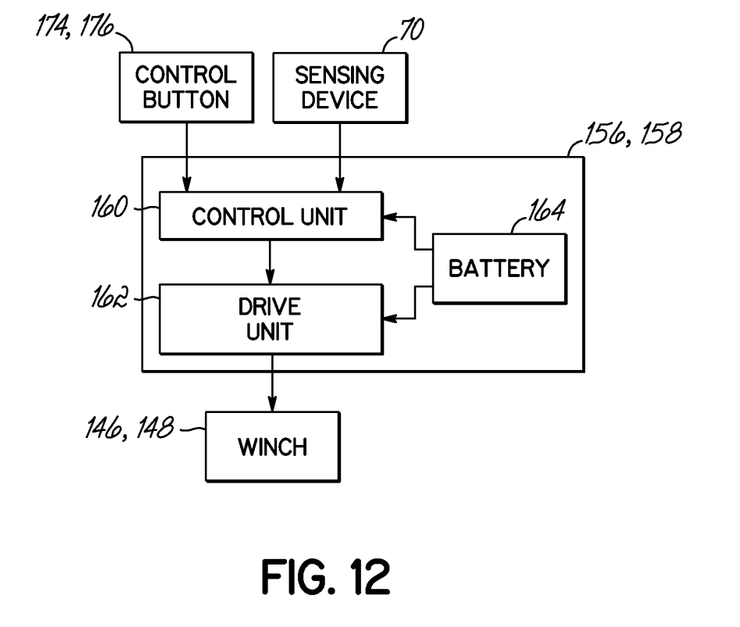
FIG. 12 is a schematic representation of the control system of the walking assistant of FIG. 11.

In reference to FIG. 11, the invention also contemplates a walking system 140 to assist a user to walk. The walking system 140 includes a pair of left and right crutches 142, 144 and a pair of winches 146, 148 mounted to the bottom portion of the crutches 142, 144. Each winch 146, 148 has a strap 150, 152 configured to be removably connected to a pair of belts 154 wrapped around the legs of the user. Similar to what is shown in FIG. 9, each strap 150, 152 has the stop-motion limit member 68 adapted to engage a sensing device, such as the limit switch 70 (not shown in FIG. 11). A housing 156, 158 is positioned above respective winches 146, 148. As shown in FIG. 12, each housing 156, 158 includes a control unit 160, a drive unit 162, both of which are electrically coupled to a power supply 164, such as a battery. Each control unit 160 contains at least one microprocessor (not shown) to operate the crutches 142, 144 in at least one control mode. The microprocessors run the software which is used to control the motion of the winches 146, 148. The drive unit 162 is a power amplifier which receives command signals from the microprocessors in the control unit 160 and then sends power to the winches 146, 148 as commanded. Each housing 156, 158 has an on-off button 166, 168 which is configured to enable or disable power from the battery 164 to the control unit 160 and the drive unit 162. Each housing 156, 158 further includes a USB interface 170, 172 for connecting the control unit 160 to a computer or mobile device for updating the software on the control unit 160, such as how predetermine length of strap 150, 152 to release from the winches 146, 148. Each crutch 142, 144 has a control button 174, 176 that is connect to the control unit 160 via cables 178, 180. Each control button 174, 176 is position to be actuated by the user's hand.

To use the walking system 140, the user turns on the power by actuating the on-off buttons 166, 168. The control unit 160 then performs a calibration routine and releases a predetermined portion of strap 150, 152 from winches 146, 148. The user would then extend the right crutch 142 forward a distance equal to or nearly equal to the predetermined portion of strap 150. The user would actuate control button 174 on right crutch 142, which instructs the control unit 160 to command the drive unit 162 to energize right winch 146. The right winch 146 would pull in strap 150 and thereby pulling the user's right leg forward. The right winch 146 continues to pull in the strap 150 until the stop-motion limit member 68 engages limit switch 70 and the right winch 146 stops and then releases a predetermined length of strap 150. The process for pulling the left leg forward would be substantially the same as the process for pulling the right leg forward. The user would then extend the left crutch 144 forward a distance equal to or nearly equal to the predetermined portion of strap 152. The user would actuate control button 176 on left crutch 144, which instructs the control unit 160 to command the drive unit 162 to energize left winch 148. The left winch 148 would pull in strap 152 and thereby pulling the user's left leg forward. The left winch 148 continues to pull in the strap 152 until the stop-motion limit member 68 engages limit switch 70 and the left winch 148 stops and then releases a predetermined length of strap 152. This sequence could be repeated by the user as needed to travel a desired distance. In addition, the user could begin the process by extending the left leg first, followed by the right leg.

While the present invention has been illustrated by the description of specific embodiments thereof, and while these embodiments have been described in considerable detail, they are not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A robotic walker comprising:
a frame having a front and a back;
a pair of motorized drive wheels configured to support the front of the frame;
a pair of wheels configured to support the back of the frame;
a housing mounted on the frame, the housing containing a control unit operatively connected to a drive unit, the housing further containing a power supply operatively connected to the control unit and the drive unit; the drive unit being operatively connected to the pair of motorized drive wheels;
first and second winches mounted on the frame, each first and second winch having a strap that can be retracted by its respective winch, each winch being operatively connected to the drive unit, each strap having an end adapted to be removably connected to a pair of leg braces worn by a user;
a stop-motion limit member affixed to each strap from the respective first and second winches;
first and second sensing devices associated with respective first and second winches, each sensing device being configured to stop the retraction of the respective straps by the first and second winches when the stop-motion limit member engages the respective sensing device; and
a first control button operatively connected to the control unit,
wherein the control unit is configured to operate the robotic walker in at least one control mode and the first control button being operable to start the at least one control mode.

2. The robotic walker of claim 1 further comprising:
a second control button operatively connected to the control unit, the second control button operable to stop the at least one control mode started by the first control button.

3. The robotic walker of claim 1, wherein the control unit is further configured to operate the robotic walker in either an automatic control mode or a manual control mode,
wherein the housing includes a touch screen control panel, the touch screen control panel having first and second buttons, the first button operable to select an automatic control mode and the second button operable to select a manual control mode.

4. The robotic walker of claim 3, wherein when the automatic control mode is selected and the first control button starts the automatic control mode, the first winch retracts a portion of its respective strap and then stops, the second winch then retracts a portion of its respective strap and then stops, and then the motorized drive wheels move the robotic walker forward a predetermined distance.

5. The robotic walker of claim 3, wherein the touch screen control panel further includes third and fourth buttons, the third button operable when actuated to cause the robotic walker to move forward, the fourth button operable when actuated to cause the robotic walker to move backwards.

6. The robotic walker of claim 1, further comprising:
third and fourth winches mounted on the frame, each third and fourth winch having a strap that can be retracted by its respective winch, each winch being operatively connected to the drive unit, each strap having an end adapted to be removably connected to the pair of leg braces worn by the user.

7. The robotic walker of claim 6, wherein the control unit is further configured to operate the robotic walker in either an automatic control mode or a manual control mode,
wherein the housing includes a touch screen control panel, the touch screen control panel having first and second buttons, the first button operable to select an automatic control mode and the second button operable to select a manual control mode.

8. The robotic walker of claim 7, wherein when the automatic control mode is selected and the first control button starts the automatic control mode, the first and third winches retract a portion of their respective straps and then stops, the second and fourth winches then retract a portion of their respective straps and then stops, and then the motorized drive wheels move the robotic walker forward a predetermined distance.

9. The robotic walker of claim 6, further comprising:
a stop-motion limit member affixed to each strap from the respective first, second, third, and fourth winches; and
first, second, third, and fourth sensing devices associated with respective first, second, third, and fourth winches, each sensing device being configured to stop the retraction of the respective straps by the first, second, third, and fourth winches when the stop-motion limit member engages the respective sensing device.

10. A robotic walker comprising:
a frame having a front and a back;
a pair of motorized drive wheels configured to support the front of the frame;
a pair of wheels configured to support the back of the frame;
a housing mounted on the frame, the housing containing a control unit operatively connected to a drive unit, the housing further containing a power supply operatively connected to the control unit and the drive unit; the drive unit being operatively connected to the pair of motorized drive wheels;
first and second winches mounted on the frame, each first and second winch having a strap that can be retracted by its respective winch, each winch being operatively connected to the drive unit, each strap having an end adapted to be removably connected to a pair of leg braces worn by a user;
a first control button operatively connected to the control unit,
wherein the control unit is configured to operate the robotic walker in at least one control mode and the first control button being operable to start the at least one control mode,
wherein the control unit is further configured to operate the robotic walker in either an automatic control mode or a manual control mode,
wherein the housing includes a touch screen control panel, the touch screen control panel having first and second buttons, the first button operable to select an automatic control mode and the second button operable to select a manual control mode,
wherein when the automatic control mode is selected and the first control button starts the automatic control mode, the first winch retracts a portion of its respective strap and then stops, the second winch then retracts a portion of its respective strap and then stops, and then the motorized drive wheels move the robotic walker forward a predetermined distance.

11. The robotic walker of claim 10 further comprising:
a second control button operatively connected to the control unit, the second control button operable to stop the at least one control mode started by the first control button.

12. The robotic walker of claim 10, wherein the touch screen control panel further includes third and fourth buttons, the third button operable when actuated to cause the robotic walker to move forward, the fourth button operable when actuated to cause the robotic walker to move backwards.

13. The robotic walker of claim 10, further comprising:
third and fourth winches mounted on the frame, each third and fourth winch having a strap that can be retracted by its respective winch, each winch being operatively connected to the drive unit, each strap having an end adapted to be removably connected to the pair of leg braces worn by the user.

14. The robotic walker of claim 13, wherein the control unit is further configured to operate the robotic walker in either an automatic control mode or a manual control mode,
wherein the housing includes a touch screen control panel, the touch screen control panel having first and second buttons, the first button operable to select an automatic control mode and the second button operable to select a manual control mode.

15. The robotic walker of claim 14, wherein when the automatic control mode is selected and the first control button starts the automatic control mode, the first and third winches retract a portion of their respective straps and then stops, the second and fourth winches then retract a portion of their respective straps and then stops, and then the motorized drive wheels move the robotic walker forward a predetermined distance.

16. A robotic walker comprising:
a frame having a front and a back;

a pair of motorized drive wheels configured to support the front of the frame;

a pair of wheels configured to support the back of the frame;

a housing mounted on the frame, the housing containing a control unit operatively connected to a drive unit, the housing further containing a power supply operatively connected to the control unit and the drive unit; the drive unit being operatively connected to the pair of motorized drive wheels;

first, second, third, and fourth winches mounted on the frame, each first, second, third, and fourth, winch having a strap that can be retracted by its respective winch, each winch being operatively connected to the drive unit, each strap having an end adapted to be removably connected to a pair of leg braces worn by a user;

a first control button operatively connected to the control unit, wherein the control unit is configured to operate the robotic walker in at least one control mode and the first control button being operable to start the at least one control mode, wherein the control unit is further configured to operate the robotic walker in either an automatic control mode or a manual control mode, wherein the housing includes a touch screen control panel, the touch screen control panel having first and second buttons, the first button operable to select an automatic control mode and the second button operable to select a manual control mode, wherein when the automatic control mode is selected and the first control button starts the automatic control mode, the first and third winches retract a portion of their respective straps and then stops, the second and fourth winches then retract a portion of their respective straps and then stops, and then the motorized drive wheels move the robotic walker forward a predetermined distance.

17. The robotic walker of claim 16 further comprising:

a second control button operatively connected to the control unit, the second control button operable to stop the at least one control mode started by the first control button.

* * * * *